United States Patent
Corbeil et al.

(10) Patent No.: US 6,883,194 B2
(45) Date of Patent: Apr. 26, 2005

(54) METHOD AND APPARATUS FOR POSITIONING A PATIENT ON A TABLE FOR A MEDICAL PROCEDURE ON A BREAST

(75) Inventors: Luc Corbeil, Ste-Anne-des-Lacs (CA); Peter Marin, Kanata (CA); Mario Gagnon, Montreal (CA); Benoît Orban, St-Lambert (CA); Christian Pilon, Montreal (CA)

(73) Assignee: Art Advanced Research and Technology Inc., St-Laurent (CA)

( * ) Notice: Subject to any disclaimer, the term of this patent is extended or adjusted under 35 U.S.C. 154(b) by 0 days.

(21) Appl. No.: 10/290,476

(22) Filed: Nov. 8, 2002

(65) Prior Publication Data

US 2004/0088791 A1 May 13, 2004

(51) Int. Cl.$^7$ .............................................. A61B 6/04
(52) U.S. Cl. ............................................. 5/601; 378/37
(58) Field of Search .................... 5/601, 632, 731, 5/735; 600/407; 378/37, 209

(56) References Cited

U.S. PATENT DOCUMENTS

| | | | | |
|---|---|---|---|---|
| 2,182,861 A | * | 12/1939 | Albert ............................ | 5/722 |
| 3,165,630 A | | 1/1965 | Bielat et al. | |
| 3,973,126 A | | 8/1976 | Redington et al. | |
| 4,015,836 A | * | 4/1977 | Redington et al. ................ | 5/601 |
| 4,063,097 A | * | 12/1977 | Barrett et al. ................... | 378/18 |
| 4,107,531 A | * | 8/1978 | Garratt et al. ................... | 378/16 |
| 4,157,472 A | * | 6/1979 | Beck et al. ...................... | 378/4 |
| 4,341,222 A | * | 7/1982 | Gardineer et al. ............. | 600/437 |
| 5,078,142 A | * | 1/1992 | Siczek et al. .................. | 600/407 |
| 5,289,520 A | * | 2/1994 | Pellegrino et al. ............. | 378/37 |
| 5,409,497 A | | 4/1995 | Siczek et al. | |
| 5,415,169 A | | 5/1995 | Siczek et al. | |
| 5,426,685 A | * | 6/1995 | Pellegrino et al. ............. | 378/87 |
| 5,564,438 A | | 10/1996 | Merchant | |
| 5,569,266 A | | 10/1996 | Siczek | |
| 5,609,152 A | | 3/1997 | Pellegrino et al. | |
| 5,692,511 A | * | 12/1997 | Grable ............................ | 600/425 |
| 5,720,061 A | * | 2/1998 | Giori et al. ...................... | 5/735 |
| 5,735,264 A | * | 4/1998 | Siczek et al. .................. | 600/408 |
| 5,803,912 A | * | 9/1998 | Siczek et al. .................. | 600/407 |
| 5,855,554 A | * | 1/1999 | Schneider et al. .............. | 600/407 |
| 6,022,325 A | * | 2/2000 | Siczek et al. .................. | 600/568 |
| 6,185,768 B1 | * | 2/2001 | Schlechter ..................... | 5/632 |
| 6,195,580 B1 | * | 2/2001 | Grable ............................ | 600/473 |
| 6,367,104 B1 | * | 4/2002 | Falbo et al. ................... | 5/601 |
| 6,407,420 B1 | * | 6/2002 | Yamanaka et al. ........... | 257/296 |
| 6,419,390 B1 | * | 7/2002 | Landis-Lowell ............. | 378/209 |
| 6,557,196 B1 | * | 5/2003 | Falbo et al. ................... | 5/601 |
| 6,662,042 B1 | * | 12/2003 | Grable ............................ | 600/473 |
| 6,738,658 B1 | * | 5/2004 | Wake et al. ................... | 600/431 |
| 2002/0056161 A1 | * | 5/2002 | Falbo et al. ................... | 5/601 |
| 2004/0081273 A1 | * | 4/2004 | Ning .............................. | 378/37 |
| 2004/0088791 A1 | * | 5/2004 | Corbeil et al. ................. | 5/601 |
| 2004/0103477 A1 | * | 6/2004 | Gagnon et al. ................ | 5/621 |

FOREIGN PATENT DOCUMENTS

| | | | | |
|---|---|---|---|---|
| DE | 2922443 A1 | * | 12/1980 | ..................... 5/735 |
| FR | 2 653 005 | | 4/1991 | |
| GB | 2 277 664 A | | 6/1993 | |
| WO | WO 98/55013 | | 12/1998 | |
| WO | WO 01/35929 A1 | | 5/2001 | |

* cited by examiner

*Primary Examiner*—Robert G. Santos
(74) *Attorney, Agent, or Firm*—James Anglehart; Alexandra Daoud; Ogilvy Renault

(57) ABSTRACT

There is provided a table for positioning a patient for a medical procedure on a breast, the table comprising: a supporting platform having a back end for supporting the patient's legs and a front end for supporting the patient's torso while the patient is in a prone position, and a cavity at the front end for allowing the breast and a surrounding axilla region to be pendantly suspended therethrough; wherein the table has a lateral depression for allowing an arm and a shoulder adjacent to the breast to extend over the table and be lowered such that skin from the axilla region is relaxed and extends through the cavity, and the table is configured to provide the depression on each side of the cavity in a position where a right shoulder would be when a right breast.

25 Claims, 4 Drawing Sheets

METHOD AND APPARATUS FOR POSITIONING A PATIENT ON A TABLE FOR A MEDICAL PROCEDURE ON A BREAST

CROSS-REFERENCE TO RELATED APPLICATION

The application is cross-referenced to U.S. patent application entitled "Method and Apparatus for Optical Imaging" filed simultaneously herewith and with agent docket number 15818-35us.

FIELD OF THE INVENTION

The invention relates to a table for positioning a patient when performing breast imaging, scanning, and biopsies. More specifically, it relates to features of the table that can improve the volume of tissue captured by the imaging/scanning apparatus and the comfort of the patient throughout the medical procedure.

BACKGROUND OF THE INVENTION

Certain medical procedures, such as breast biopsies, must be done with the patient in a face down prone position. There are also imaging and scanning procedures that are done in a prone position. There are several variations of tables that currently exist for these procedures.

For example, U.S. Pat. No. 5,569,266 issued to Siczek discloses a magnetic resonance imaging device useful for guiding a medical instrument, such as a biopsy needle. The patient is positioned on a table top having an opening through which the patient's breast pendulantly projects. The pendulant breast is immobilized by a basket. The drawbacks of this table are in the volume of tissue that can project through the basket and the general comfort of the patient.

Another example is U.S. Pat. No. 5,609,152 issued to Pellegrino et al. for a prone position stereotactic mammography needle biopsy apparatus and a method for using the same. The table disclosed by Pellegrino et al. comprises a space for an arm to come down beside the table. A drawback of this design is that there is no room for the axilla region to be accessed. This is a serious drawback as a large proportion of tumors in breast cancer are found in the tissue in the axilla region.

Moreover, since new imaging and scanning systems are coming out that require patients to lie on a table for a substantial amount of time, there is a need to improve the general comfort of the patient for medical procedures that are sometimes unpleasant.

SUMMARY OF THE INVENTION

Accordingly, an object of the present invention is to overcome the drawbacks of the prior art.

Yet another object of the present invention is to improve the general comfort of the patient for medical procedures on breasts.

According to a first broad aspect of the present invention, there is provided a table for positioning a patient for a medical procedure on a breast, the table comprising: a supporting platform having a back end for supporting the patient's legs and a front end for supporting the patient's torso while the patient is in a prone position, and a cavity at the front end for allowing the breast and a surrounding axilla region to be pendantly suspended therethrough; wherein the table has a lateral depression for allowing an arm and a shoulder adjacent to the breast to extend over the table and be lowered such that skin from the axilla region is relaxed and extends through the cavity, and the table is configured to provide the depression on each side of the cavity in a position where a right shoulder would be when a right breast is in the cavity and a left shoulder would be when a left breast is in the cavity.

Preferably, a lateral depression is provided on one side of the table and a movable portion of the table rotates to the other side of the table so as to provide the depression on the opposite side when an opposite breast is placed in the cavity. The rotation is done with a rotating plate engaged into the supporting platform, and in conjunction with a headrest that also rotates laterally. Also preferably, the cavity is adjustable in size and position.

According to a second broad aspect of the present invention, there is provided a table for positioning a patient for a medical procedure on a breast, the table comprising: a supporting platform having a back end for supporting the patient's legs and a front end for supporting the patient's torso while the patient is in a prone position, and a cavity at the front end for allowing the breast and a surrounding axilla region to be pendantly suspended therethrough; wherein the cavity is substantially pear-shaped such that a larger portion is for the breast and a narrower portion is for the axilla region, and the cavity is positioned at an angle such that the narrower portion faces an outer side of the supporting platform.

Preferably, the table comprises a lateral depression that is provided on one side of the table and a movable portion of the table rotates to the other side of the table so as to provide the depression on the opposite side when an opposite breast is placed in the cavity. The rotation is done with a rotating plate engaged into the supporting platform, and in conjunction with a headrest that also rotates laterally. Also preferably, the pear-shaped cavity is rotated such that it is always angled in a way that the narrower portion faces the outer edge of the table.

According to a third broad aspect of the present invention, there is provided a method for positioning a patient on a table for a medical procedure on a breast, the method comprising: placing the patient face down in a prone position on a supporting platform such that the patient's legs and torso are supported; providing a cavity in the supporting platform such that the breast and a surrounding axilla region is pendantly suspended therethrough; extending an arm and a shoulder adjacent to the breast over the table such that skin from the axilla region is relaxed and extends through the cavity, wherein a left arm and shoulder is extended over the table on a left side of the cavity when a left breast is in the cavity and a right arm and shoulder is extended over the table on a right side of the cavity when a right breast is in the cavity.

Preferably, the arm extended over the table is adjusted in height and in position on an armrest provided for the elbow and forearm to rest on. The head and feet are also adjusted in height for comfort purposes. The cavity is substantially pear-shaped and is rotated such that when a left breast is in the cavity, the narrower portion is facing the left side of the table and when a right breast is in the cavity, the narrower portion is facing the right side of the table.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

Figure 1:
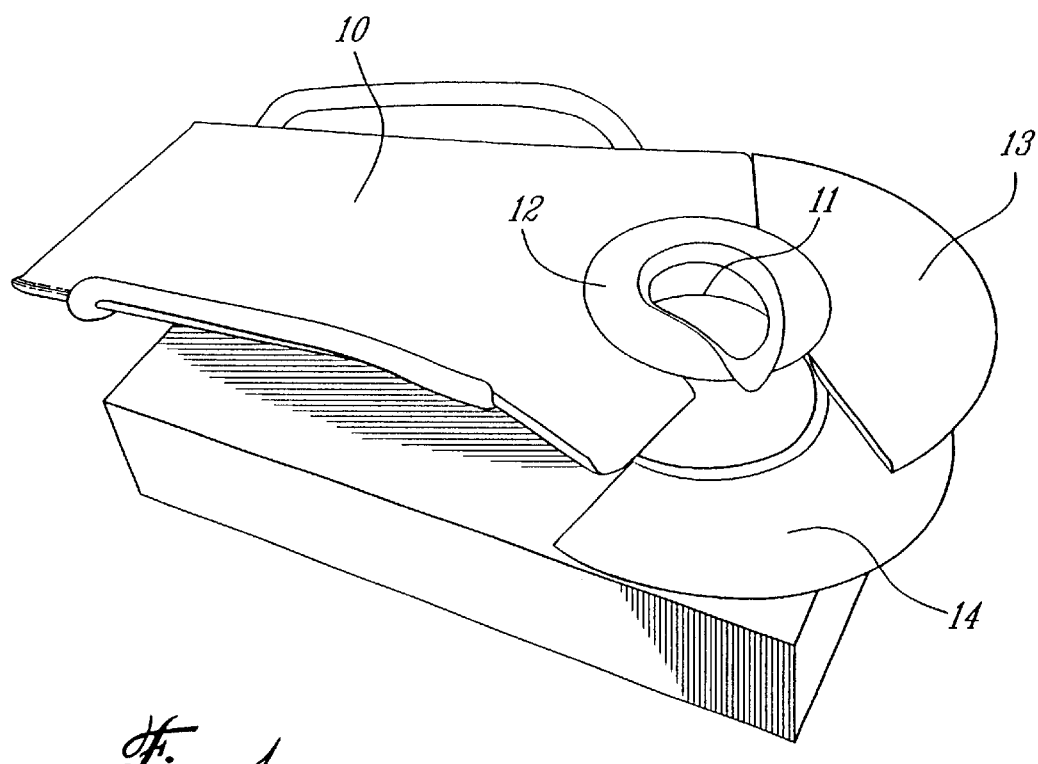
FIG. 1 is a preferred embodiment of the table in accordance with the present invention.

FIG. 1 shows a preferred embodiment for the table. The table comprises a supporting platform 10 having a back end and a front end for supporting the patient's legs and torso, respectively. The patient lies face down on the table, slightly off center, and places a breast inside the cavity 11 present in the front end of the supporting platform 10. The breast is pendantly suspended within the cavity 11. The table has a lateral depression for allowing the arm and shoulder adjacent to the breast to extend over the table.

In the embodiment shown in FIG. 1, the cavity is substantially pear-shaped.

That is to mean that the cavity comprises a wide and a narrow portion, such that the wide portion is for the breast to be suspended therethrough and the narrow portion is for the axilla region adjacent to the breast to be suspended therethrough. The shape of the cavity is such that a maximum possible volume of tissue can be exposed below the table. This way, access to the regions of interest is facilitated.

The table shown in FIG. 1 can be used to perform a medical procedure on a left or a right breast. The cavity is present in a disc plate 12 in the front end of the supporting platform 10. For imaging of the left breast, the cavity 11 must be rotated such that the narrow portion is facing towards the left side of the table in order to receive the left axilla region of the patient. The rotation of the disc 12 can be done manually or remotely with a set of controls. The headrest 13 must also be moved such that the space provided for the arm of the patient is on the left side of the table. As can be seen from the figure, the headrest 13 is independent of the supporting platform 10 and can be slid to the opposite side. This can also be done either manually or remotely with a set of controls.

In optical imaging, it is desirable to obtain a simple geometry of the object being imaged such that mathematical algorithms can be used to produce the actual image. One way to do this is to use a pair of parallel plates that compress the breast into a rectangular slab and produce a parallelepiped. the plates are also used to stabilize the breast and prevent motion during the imaging. When stabilizing plates are used to compress the breasts and scan an image, a circular shape is ideal for the cavity when the compression is at 0° and 90° with respect to the table. However, a pear-shaped or oval cavity is preferred when compressing the breast at around 45° with respect to the table in order to properly access the tissue in the axilla region. Therefore, the disc plate 12 seen in FIG. 1 is removable and can be replaced by a similar disc plate with a cavity that is circular. Furthermore, the circular cavities may vary in size to accommodate breasts of different sizes.

An armrest 14 can also be seen in the figure. The armrest 14 is below the level of the table and serves to support the elbow and forearm of the patient that is adjacent to the breast suspended in the cavity 11. The armrest 14 is adjustable in height to accommodate patients of different sizes and place the shoulder at the ideal level such that the patient is comfortable enough to remain in a fixed position for a substantially long amount of time. The supporting platform 10 is also slightly inclined such that the legs and feet are at a lower level than the head and torso. This is also for patient comfort and provides the patient with a better sense of stability in the prone position.

Figure 2A:
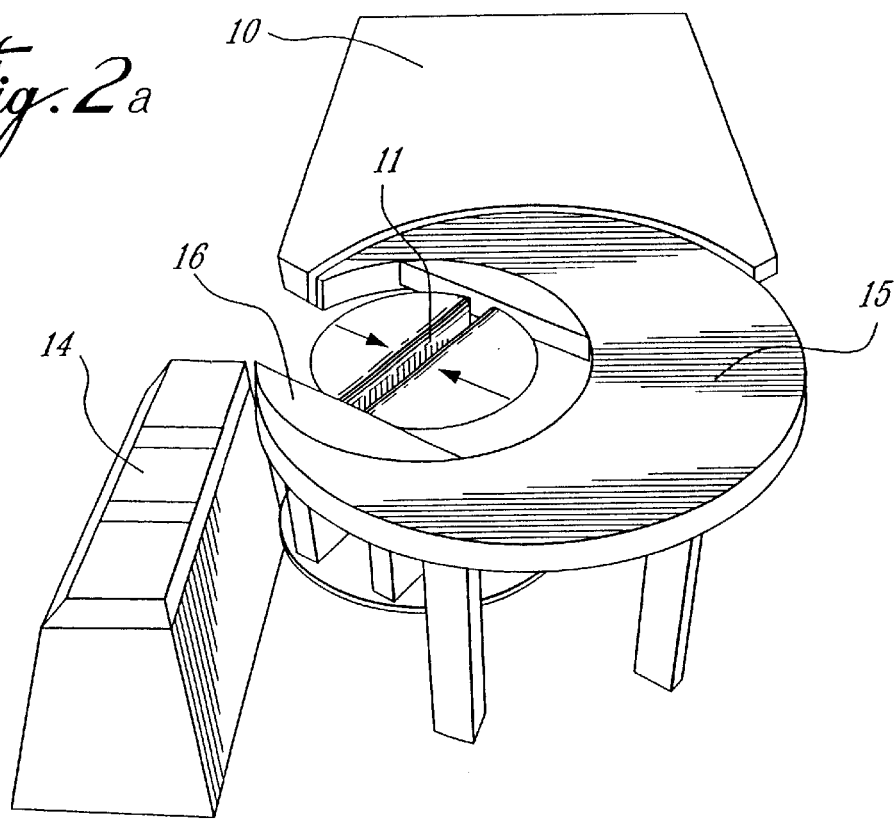
FIG. 2 is an alternative embodiment of the table in accordance with the present invention.
Figure 2B:
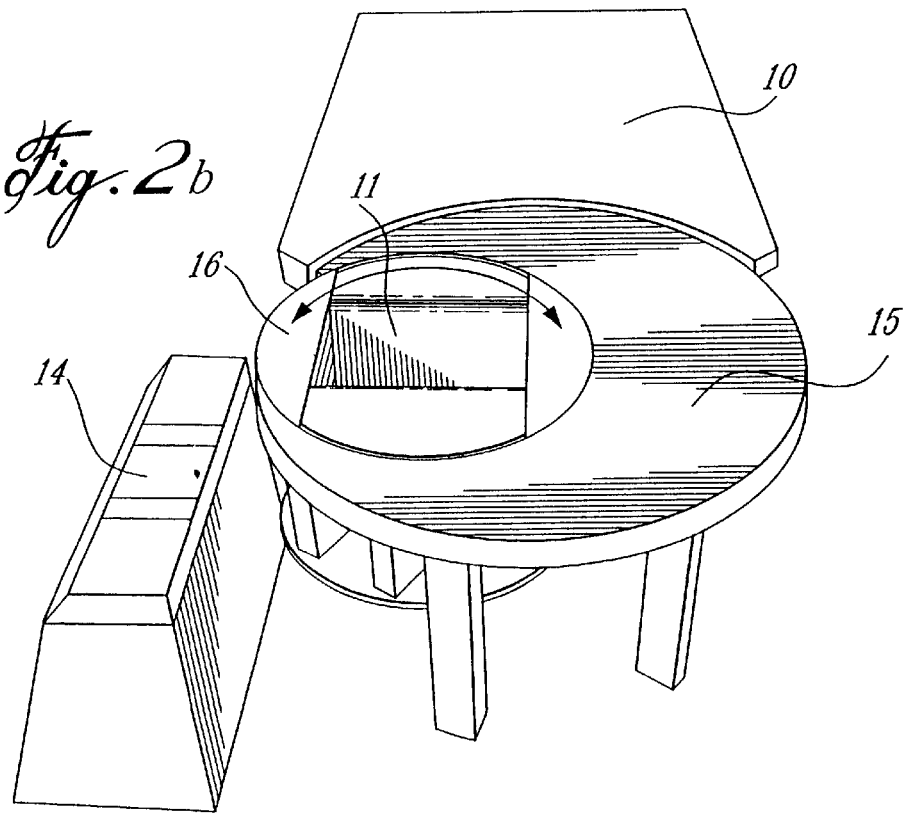

FIG. 2 shows an alternative embodiment to providing a space for the arm on a left and a right side of the table. A supporting platform 10 is still present to support the legs and torso of the patient. However, a large disc 15 is engaged into the supporting platform 10. Within this large disc 15 is a smaller disc 16 with the cavity 11 for the breast. The larger disc 15 rotates such that the opening for the breast is on the left or the right side of the table, depending on the breast in question. The cavity 11 for the breast is closer to the side than in the previous embodiment, shown in FIG. 1.

The design of the smaller disc 16 is such that the breast can be scanned or imaged in at least three directions. Two parallel, vertical, stabilizing plates compress the breast at 0° (the plates move along the axes of the table), 90° (the plates move perpendicular to the axes of the table), and 45° (the plates move diagonally). The plates, which are seen as two compression members in the figure, form a rectangular cavity and can accommodate breasts of varying sizes. The two plates can move inwards for compression, as well as up, down, and rotate with respect to the rest of the platform. The smaller disc 16 is formed of at least two separate pieces that surround the cavity 11. One of the pieces can be removed to leave a space for the axilla and underarm region, providing a lateral depression on a left or a right side of the table, depending on the position of the larger disc 15. An armrest 14 is also present to support the forearm and elbow when the axilla region is exposed through the cavity 11.

The design of the larger disc 15 is possible without the smaller disc 16 within it. A regular cavity is present within the larger disc 15, the cavity being fixed in size and shape. This embodiment can be used for biopsies, wherein it is unnecessary to compress the breast at different angles because images are not being taken of the breast. The biopsy equipment can easily be placed underneath the table and used in conjunction with it.

Alternatively, a pear-shaped cavity may be present in the larger disc. The cavity is to be angled at approximately 45° below the horizontal axis of the disc. When the disc is rotated, the cavity is still angled at approximately 45° of the horizontal axis, but on the opposite side of the table. In this case, compression plates may be independent from the table and be provided beneath the table. A space on adjacent to the cavity is to be provided for the arm if the smaller disc plate is not within the larger disc plate.

Figure 3:
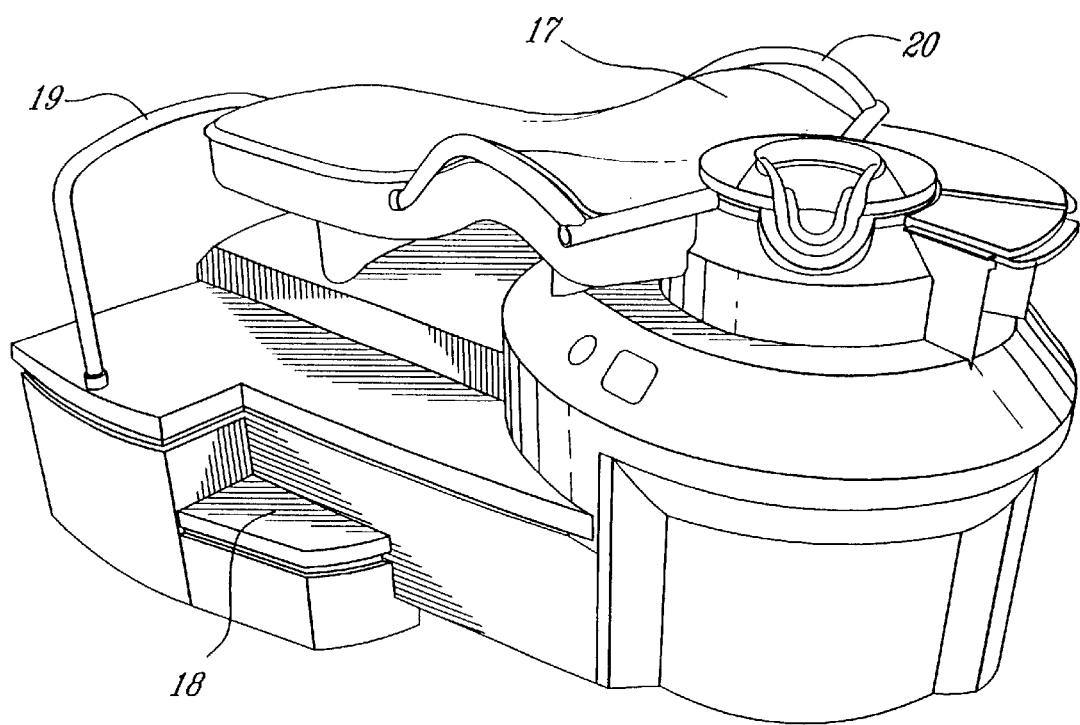
FIG. 3 is another embodiment of the table in accordance with the present invention.

FIG. 3 is a preferred embodiment of the apparatus in accordance with the present invention. From the figure, it can be seen that the supporting platform is not flat, but instead comprises concave and convex curves that are specially designed to increase patient comfort. The central area of the supporting platform is upwardly winged on each side so as to nest the patient within the curve formed by the wings 17. This creates a sensation of security and eliminates the possibility of rolling off the table. Steps 18 are adjacent to the supporting platform to facilitate mounting of the patient. A banister 19 and handles 20 are also provided to facilitate the mounting and allow the patient to ease herself onto the table comfortably.

Figure 4:
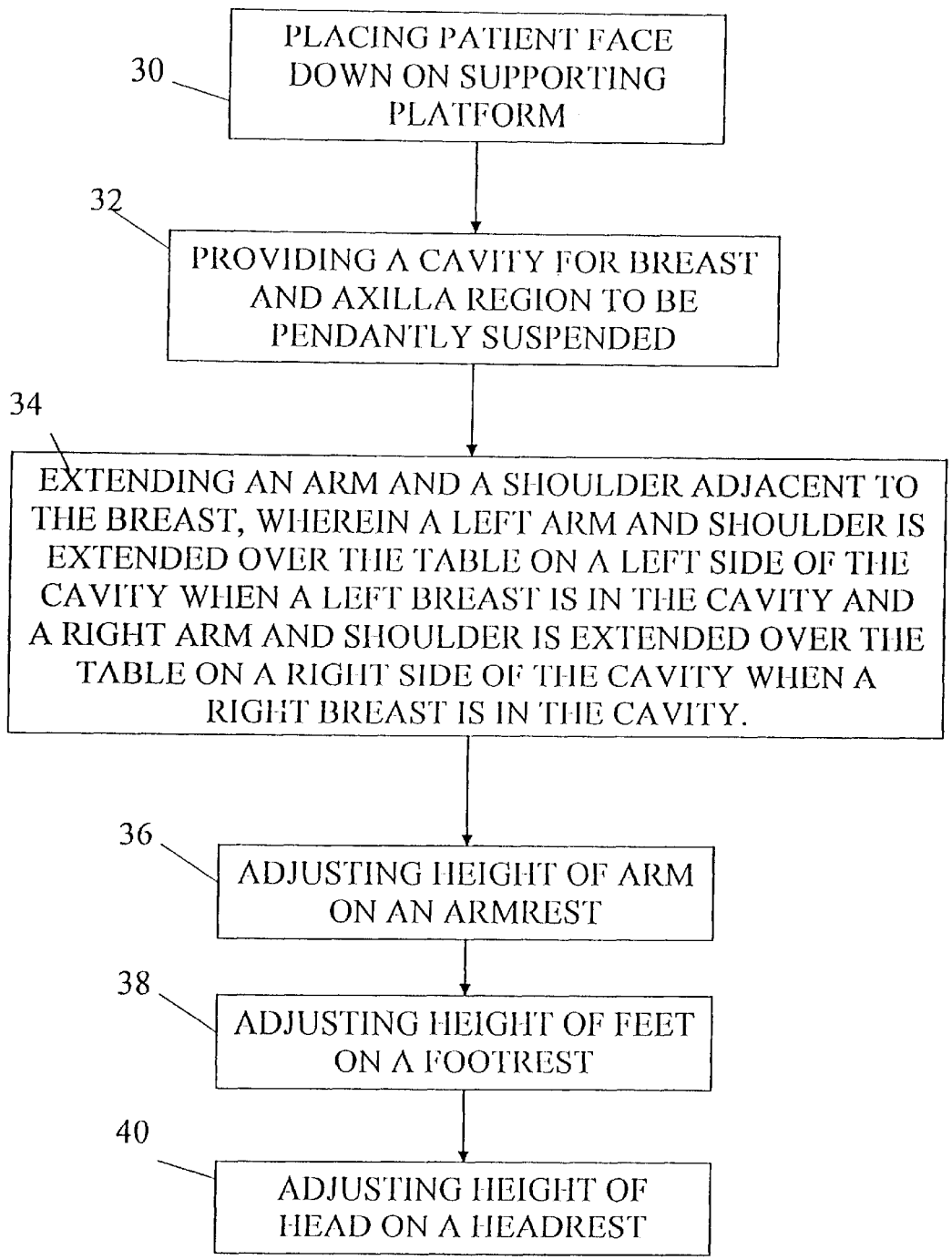
FIG. 4 is a flowchart of the method in accordance with the present invention.

FIG. 4 corresponds to a flow chart according to the method of the present invention of positioning a patient on a table for a medical procedure on a breast. The first step is to place the patient face down on the supporting platform 30. A cavity is provided for the breast and axilla region to be pendantly suspended therethrough 32. An arm and shoulder of the patient adjacent to the breast is extended over the table, wherein a left arm and shoulder is extended over the table on a left side of the cavity when a left breast is in the cavity and a right arm and shoulder is extended over the right side of the table when a right breast is in the cavity 34. The height of the arm and shoulder is adjusted 36 by adjusting the position of the elbow and forearm on an armrest which is provided below the supporting platform. The arm can be supported by being extended upwards and bent inwards towards the head or simply by being extended parallel to the body. The feet of the patient are also adjusted in height 38 by elevating them using a footrest. The head is then adjusted in height 40 on a headrest.

When placing the patient face down on the supporting platform 30, the patient may be placed in an inclined position such that the feet are lower towards the ground than the upper body. The cavity provided may be substantially pear-shaped such that a narrower portion is for the axilla region and a larger portion is for the breast. This pear-shaped cavity is rotated from a left side of the table to a right side of the table, and vice-versa, such that the narrower portion is always angled towards the outer edge of the table, whether a left or a right breast is in the cavity.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A table for positioning a patient for a medical procedure on a breast, the table comprising;
   a supporting platform having a back end for supporting said patient's legs and a front end for supporting said patient's torso while said patient is in a prone position, and a cavity at said front end for allowing said breast and a surrounding axilla region to be pendantly suspended therethrough; and
   a rotating mechanism in said front end to provide a lateral depression on each side of said cavity in a position where a right shoulder would be when a right breast is in the cavity and a left shoulder would be when a left breast is in the cavity, said lateral depression allowing an arm and a shoulder adjacent to said breast to extend over said table and be lowered such that skin from said axilla region is relaxed and extends through said cavity.

2. A table as claimed in claim 1, wherein said rotating mechanism comprises a disc plate engaged into said front end and housing said cavity, said disc plate pivotable about an axis such that said lateral depression is provided on a left aide of said table when a left breast is in said cavity and on a right side of said table when a right breast is in said cavity.

3. A table as claimed in claim 2, wherein said disc plate comprises a smaller disc plate housing said cavity, wherein said smaller disc plate is adjacent to said lateral depression and is provided on a left side of said table when a left breast is in said cavity and on a right side of said table when a right breast is in said cavity, and said smaller disc plate is moveable about a plurality of axes independently from said disc plate such that said cavity is adjustable in position and size.

4. A table as claimed in claim 3, wherein said smaller disc plate is comprised of two compression members having linear movement relative to each other for adjusting said cavity in size, at least one of said compression members is removable to provide said lateral depression, and wherein said compression members have linear movement relative to said disc plate.

5. A table as claimed in claim 1, further comprising a headrest adjacent to said front end for supporting a heed of said patient while in said prone position.

6. A table as claimed in claim 5, wherein said headrest is configured to be laterally displaceable with respect to said supporting platform in order to provide said lateral depression on each side of said cavity.

7. A table as claimed in claim 1, further comprising an armrest for positioning and supporting a forearm such that a shoulder adjacent to said axilla region is at a desired height, and wherein said armrest is lower than said supporting platform.

8. A table as claimed in claim 1, further comprising a footrest to elevate said patient's feet such that additional comfort is provided when remaining in a prone position for an extended period of time.

9. A table as claimed in claim 1, wherein said supporting platform is inclined such that said back end is lower than said front end in order to provide additional comfort for said patient.

10. A table for positioning a patient for a medical procedure on a breast, the table comprising:
    a supporting platform having a back end for supporting said patient's legs and a front end for supporting said patient's torso while said patient is in a prone position, and a cavity at said front end for allowing said breast and a surrounding axilla region to be pendantly suspended therethrough;
    wherein said cavity is substantially pear-shaped such that a larger portion is for the breast and a narrower portion is for the axilla region, and said cavity is positioned at an angle such that said narrower portion faces an outer side of said supporting platform.

11. A table as claimed in claim 10, wherein said table has a lateral depression for allowing an arm and a shoulder adjacent to said breast to extend over said table and be lowered such that skin from said axilla region is relaxed and extends through said cavity, said depression adjacent to said narrower portion of said cavity.

12. A table as claimed in claim 11, wherein said table is configured to provide said depression on each side of said cavity in a position where a right shoulder would be when a right breast is in the cavity and a left shoulder would be when a left breast is in the cavity, and wherein said table is configured such that said pear-shaped cavity is displaced to provide said narrower portion on a left side of said table when a left breast is in said cavity and on a right side of said table when a right breast is in said cavity.

13. A table as claimed in claim 12, wherein said supporting platform further comprises a disc plate engaged into said front end and housing said cavity, said disc plate pivotable about an axis such that said cavity is rotated to a left side of said table when a left breast is in said cavity and a right side of said table when a right breast is in said cavity.

14. A table as claimed in claim 10, further comprising a headrest adjacent to said front end for supporting a head of said patient while in said prone position.

15. A table as claimed in claim 14, wherein said headrest is configured to be laterally displaceable with respect to said supporting platform in order to provide said depression on each side of said cavity.

16. A table as claimed in claim 11, further comprising an armrest for positioning and supporting a forearm such that a shoulder adjacent to said axilla region is at a desired height, and wherein said armrest is lower than said supporting platform.

17. A table as claimed in claim 10, further comprising a footrest to elevate said patient's feet such that additional comfort is provided when remaining in a prone position for an extended period of time.

18. A table as claimed in claim 11, wherein said supporting platform is inclined such that said back end is lower than said front end in order to provide additional comfort for said patient.

19. A method for positioning a patient on a table for a medical procedure on a breast, the method comprising:

placing said patient face down in a prone position on a supporting platform such that said patient's legs and torso are supported;

providing a cavity in said supporting platform such that said breast and a surrounding axilla region is pendantly suspended therethrough;

extending an arm and a shoulder adjacent to said breast over said table such that skin from said axilla region is relaxed and extends through said cavity, wherein a left arm and shoulder is extended over said table on a left side of said cavity when a left breast is in said cavity and a right arm and shoulder is extended over said table on a right side of said cavity when a right breast is in said cavity.

20. A method as claimed in claim 19, further comprising adjusting a height of said arm and shoulder extended over said table such that a maximum volume of tissue of said breast and axilla region extends through said cavity, wherein adjusting a height comprises placing an elbow and a forearm on an armrest such that said shoulder is at a desired height.

21. A method as claimed in claim 19, further comprising adjusting a height of said patient's head such that additional comfort is provided.

22. A method as claimed in claim 19, further comprising elevating said patient's feet such that additional comfort is provided.

23. A method as claimed in claim 19, wherein said placing said patient face down in a prone position comprises placing said patient in an inclined position such that said patient's legs are lower than said patient's torso.

24. A method as claimed in claim 19, wherein said providing a cavity further comprises providing a cavity that is substantially pear-shaped, such that a narrower portion is for the axilla region and a larger portion is for the breast.

25. A method as claimed in claim 24, wherein said providing a cavity also comprises rotating said substantially pear-shaped cavity such that said narrower portion is angled towards an outer left side of said table when a left breast is in said cavity and an outer right side of said table when a right breast is in said cavity.

* * * * *